US011464726B2

(12) United States Patent
Wils et al.

(10) Patent No.: US 11,464,726 B2
(45) Date of Patent: Oct. 11, 2022

(54) 1,4: 3,6 DIANHYDROHEXITOLS FOR MOISTURISING THE SKIN

(71) Applicant: ROQUETTE FRERES, Lestrem (FR)

(72) Inventors: Daniel Wils, Morbecque (FR); Léon Mentink, Lille (FR)

(73) Assignee: ROQUETTE FRERES, Lestrem (FR)

( * ) Notice: Subject to any disclaimer, the term of this patent is extended or adjusted under 35 U.S.C. 154(b) by 0 days.

(21) Appl. No.: 16/633,536

(22) PCT Filed: Aug. 1, 2018

(86) PCT No.: PCT/FR2018/051981
§ 371 (c)(1),
(2) Date: Jan. 23, 2020

(87) PCT Pub. No.: WO2019/025730
PCT Pub. Date: Feb. 7, 2019

(65) Prior Publication Data
US 2020/0230042 A1     Jul. 23, 2020

(30) Foreign Application Priority Data

Aug. 2, 2017 (FR) ..................................... 17 57421

(51) Int. Cl.
| | | |
|---|---|---|
| *A61K 8/49* | (2006.01) | |
| *A61K 8/02* | (2006.01) | |
| *A61K 8/04* | (2006.01) | |
| *A61K 9/08* | (2006.01) | |
| *A61K 9/14* | (2006.01) | |
| *A61K 31/34* | (2006.01) | |
| *A61Q 19/00* | (2006.01) | |
| *A61K 9/00* | (2006.01) | |

(52) U.S. Cl.
CPC ............ *A61K 8/4973* (2013.01); *A61K 8/022* (2013.01); *A61K 8/04* (2013.01); *A61K 9/08* (2013.01); *A61K 9/14* (2013.01); *A61K 31/34* (2013.01); *A61Q 19/00* (2013.01); *A61K 9/0014* (2013.01); *A61K 2800/30* (2013.01)

(58) Field of Classification Search
None
See application file for complete search history.

(56) References Cited

U.S. PATENT DOCUMENTS

| | | | |
|---|---|---|---|
| 7,964,638 B2 | 6/2011 | Miura et al. | |
| 8,658,138 B2 * | 2/2014 | Graupe | A61P 17/06 424/45 |
| 2011/0117036 A1 | 5/2011 | Chaudhuri | |
| 2013/0183257 A1 | 7/2013 | Chaudhuri | |
| 2016/0199343 A1 * | 7/2016 | De Visscher | A61K 31/34 424/445 |

FOREIGN PATENT DOCUMENTS

| | | |
|---|---|---|
| CN | 103083282 A | 5/2013 |
| JP | 2008081474 A | 4/2008 |

OTHER PUBLICATIONS

The English translation of the International Search Report, dated Nov. 6, 2018, in the corresponding PCT Appl. No. PCT/FR2018/051981.

* cited by examiner

*Primary Examiner* — Nannette Holloman

(57) ABSTRACT

The invention relates to the non-therapeutic use of a composition comprising at least one 1,4:3,6 dianhydrohexitol for moisturising the skin, as well as to a preparation for topical use comprising at least one 1,4:3,6 dianhydrohexitol as a moisturising agent.

14 Claims, No Drawings

1,4: 3,6 DIANHYDROHEXITOLS FOR MOISTURISING THE SKIN

CROSS-REFERENCE TO RELATED APPLICATIONS

This application is a National Stage Application of PCT/FR2018/051981 filed Aug. 1, 2018, which claims priority from French Patent Application No. 17 57421, filed on Aug. 2, 2017. The priority of said PCT and French Patent Application are claimed. Each of the prior mentioned applications is hereby incorporated by reference herein in its entirety.

FIELD OF THE INVENTION

The subject of the invention is the non-therapeutic use of a composition based on 1,4:3,6-dianhydrohexitol, preferably based on isosorbide, for moisturizing the skin.

PRIOR ART

Today, the skin moisturizing agent most used in the cosmetics field is glycerol. Specifically, it is contained in a large number of cosmetic products for topical use, such as creams, lotions, shower gels and shampoos, to give them moisturizing properties. However, glycerol has a certain number of drawbacks on the sensory level when it is used in large amounts. Specifically, depending on the topical preparations chosen, a glycerol content of greater than 20%, or even only greater than 10% by weight relative to the weight of said preparation, leads to a greasy and tacky feel on the skin, which is judged to be unpleasant.

Patent application EP 1 891 929 A1 describes the use of isosorbide as an anti-wrinkle agent in cosmetic preparations for the skin such as creams or lotions. According to this application, isosorbide reduces the thickening of the epidermis induced by photoaging which results in a reduction in wrinkles. A moisturizing effect of the isosorbide is neither described nor suggested.

In view of the drawbacks of glycerol, one of the objectives of the present invention is to provide an alternative to glycerol which does not have these drawbacks of a greasy and tacky feel.

After intense research and studies using various products, in particular various polyols, the applicant has found that this objective could be achieved by choosing a particular polyol having a high moisturizing power without leaving a greasy or tacky feel on the skin.

SUMMARY OF THE INVENTION

Thus, the invention relates to the non-therapeutic use of a composition comprising at least one 1,4:3,6-dianhydrohexitol, in particular isosorbide, for moisturizing the skin and also a composition for topical use comprising a composition comprising at least one 1,4:3,6-dianhydrohexitol, this at least one 1,4:3,6-dianhydrohexitol being in particular isosorbide, as moisturizing agent.

DETAILED DESCRIPTION OF THE INVENTION

Against all expectations, 1,4:3,6-dianhydrohexitols, in particular isosorbide, proved to be skin moisturizing agents that have a good moisturizing power, both instantaneously and in a long-lasting manner. Unlike glycerol, a preparation for topical use formulated with a composition comprising at least one 1,4:3,6-dianhydrohexitol leaves a dry and powdery feel on the skin. Even when it is used in large amounts, i.e. above 10% or even above 20% by dry weight, a composition comprising at least one 1,4:3,6-dianhydrohexitol does not give rise to a greasy and tacky feel. Furthermore, and very advantageously, it provides a greater feeling of freshness than glycerol. Moreover, the applicant has noted that a preparation for topical use formulated with a composition comprising at least one 1,4:3,6-dianhydrohexitol spreads more easily on the skin and penetrates better into the skin than a control preparation formulated with glycerol.

Throughout the present application, the moisturizing power is related to the ability of a preparation for topical use to moisturize the surface layer of the epidermis: the water contained in said preparation will be transported into this layer. From a sensory point of view, it results in a feeling of freshness. This moisturizing power may for example be measured by corneometry, a scientifically recognized method for measuring the hydration of the surface layers of the skin, the use of which is explained in greater detail in the examples section.

The moisturizing power should not be confused with other properties which are measured at the surface of the skin and not in the layers of the epidermis. This is for example the case for the feel. Certain characteristics of the feel are not dependent on the moisturizing power: thus, a preparation for topical use may give rise to a greasy and tacky feel if it is for example based on glycerol, or conversely a dry and powdery feel as in the case of the invention. In certain cases, the feel may be influenced by the moisturizing power: a better hydration of the upper layer of the epidermis makes the skin softer and more elastic. But in any case, the feel refers to a property which is measured at the surface of the skin, not in the layers of the epidermis.

When these properties are the subject of examples and characterizations in the present application, the tests relating thereto clearly establish the chosen frame of reference: the surface layer of the epidermis for the moisturizing power, and the surface of the epidermis for the feel.

1,4:3,6-dianhydrohexitols, also referred to simply as dianhydrohexitols or isohexides, are products of a double internal dehydration of C6 polyols (hexitols) such as sorbitol, mannitol and iditol. In the present application, the term "1,4:3,6-dianhydrohexitol" encompasses isosorbide (1,4:3,6-dianhydrosorbitol), isomannide (1,4:3,6-dianhydromannitol), isoidide (1,4:3,6-dianhydroiditol). Also, the composition used in accordance with the invention may contain a single 1,4:3,6-dianhydrohexitol, preferably isosorbide, or any mixture of the aforementioned 1,4:3,6-dianhydrohexitols. The composition comprising at least one 1,4:3,6-dianhydrohexitol used according to the invention may be used in solid, preferably crystalline form, in particular in the form of powder or flakes, or in liquid form. In the first case, in solid form, the composition is not necessarily completely anhydrous and may therefore contain water in a small amount, in particular up to around 5% by weight. In the second case, it is generally a paste or an aqueous solution of at least one 1,4:3,6-dianhydrohexitol having a solids content that may be between 1% and 95% by weight. Preferably, for reasons of logistics costs and storage costs, but also for ease of use during the production of the preparation for topical use, a concentrated solution of 1,4:3,6-dianhydrohexitol, i.e. having a solids content of greater than 30% by weight, preferably greater than 50% by weight and better still greater than 70% by weight, will tend to be chosen. Use could in particular be made of a 1,4:3,6-dianhydrohexitol composition having a solids content of between 75% and 85% by weight.

Since 1,4:3,6-dianhydrohexitols are natural products derived from the conversion of starch, they still contain impurities such as for example caramelized sugars and products derived from thermal or Maillard reactions. This is why they are generally used in the form of a composition, of which the dry weight content essentially consists of a single 1,4:3,6-dianhydrohexitol. Within the meaning of the present invention, the expression "dry weight content essentially consists of at least one 1,4:3,6-dianhydrohexitol" is understood to mean a 1,4:3,6-dianhydrohexitol content of at least 75% by weight (dry/dry) and preferably of at least 90% by weight (dry/dry). Even though the degree of purity of the composition used in accordance with the invention or in other words its dry weight content of 1,4:3,6-dianhydrohexitol relative to the total solids content does not appear per se to be of prime importance with regard to its skin moisturizing power, it is however preferable for organoleptic, sensory or safety reasons, that its dry weight content of 1,4:3,6-dianhydrohexitol relative to the total solids content be as high as possible. For this, use will be made of a composition, of which the dry weight content consists essentially of a 1,4:3,6-dianhydrohexitol in the most purified possible form, in particular obtained following steps of distillation or crystallization.

Thus, the presence of coloring or odorous impurities such as for example caramelized sugars and products derived from thermal or Maillard reactions that some of these non-purified 1,4:3,6-dianhydrohexitol compositions may contain, will be limited to a dry weight content of less than 2%, better still less than 1% and even better still less than 0.5% relative to the total solids content of 1,4:3,6-dianhydrohexitol of the composition. Ideally, the presence of coloring or odorous impurities is less than 0.2% relative to this solids content and preferably less than 0.1% relative to this solids content. More preferentially still, the composition is colorless and is completely odor-neutral. Therefore, advantageously the composition used according to the invention will be prepared from or will comprise a composition, of which the dry weight content consists essentially of a single 1,4:3,6-dianhydrohexitol, this dry weight content being at least equal to 98%, preferably at least equal to 99% and more preferably at least equal to 99.5%.

As mentioned above, the composition used according to the invention may comprise several 1,4:3,6-dianhydrohexitols or a single 1,4:3,6-dianhydrohexitol, preferably isosorbide. This composition may be used alone or as a mixture with other products that may be of interest for the formulation of the preparation for topical use, such as in particular other moisturizing agents such as betaine, sorbitol, xylitol, glycerol or acetamidoethoxyethanol or else other products that are active or have sensory effects with respect to the skin, such as for example starch.

In the context of the present invention, use is preferably made of a composition in which the at least one 1,4:3,6-dianhydrohexitol is isosorbide. As indicated above, this may be used in solid or liquid form, preferably having a content of isosorbide at least equal to 98.5% by dry weight, preferably at least equal to 99% by dry weight and more preferentially still at least equal to 99.5% by dry weight relative to the total solids content. Preferentially, isosorbide is used in liquid form. The isosorbide range sold by the applicant company under the trade name POLYSORB® is particularly suitable for the purposes of the present invention.

According to one embodiment, the composition comprising at least one 1,4:3,6-dianhydrohexitol, in particular the composition comprising isosorbide, is incorporated into a preparation for topical use. For the purposes of the present invention, a preparation for topical use is understood to mean any composition intended to be brought into contact with human or animal skin. It may thus be a cosmetic composition, a pharmaceutical composition or a veterinary composition. Nonlimiting examples of preparations for topical use include lotions, creams, serums, gels, ointments, balms, liquid soaps or shower gels, shampoos, mousses, foundations, antiperspirants and deodorants. These preparations may comprise, in addition to the composition comprising at least one 1,4:3,6-dianhydrohexitol, other ingredients customarily used in preparations for topical use, such as for example cosmetic, pharmaceutical and/or veterinary active principles, and adjuvants such as preservatives, solubilizers or fragrances. It may also comprise other moisturizing agents such as betaine, sorbitol, xylitol, glycerol or acetamidoethoxyethanol or else other products that are active or have sensory effects with respect to the skin, such as for example starch.

Owing to its moisturizing power and its good sensory properties, the composition comprising at least one 1,4:3,6-dianhydrohexitol may be used as a complete or partial replacement for the glycerol customarily used as moisturizing agent in preparations for topical use. Preferably, it completely replaces glycerol. In this case, the preparation for topical use is free of glycerol. Alternatively, the preparation for topical use may contain glycerol at a low content, in particular less than or equal to 10%, preferably less than or equal to 5% and more preferentially still less than or equal to 1% by weight relative to the total weight of the preparation.

The total content of 1,4:3,6-dianhydrohexitol of the preparation for topical use may be between 0.1% and 50%, preferably between 1% and 40%, more preferentially still between 5% and 30% and better still between 10% and 25% by dry weight relative to the total weight of the preparation. It is understood that the term "1,4:3,6-dianhydrohexitol" in the singular in the context of the content in the preparation for topical use means that it may be the content of a single 1,4:3,6-dianhydrohexitol or of several 1,4:3,6-dianhydrohexitols.

The use of a composition comprising at least one 1,4:3,6-dianhydrohexitol as moisturizing agent has many advantages as explained above. Very particularly, the use of at least one 1,4:3,6-dianhydrohexitol as moisturizing agent has the advantage of not giving a greasy and/or tacky feel but a dry and powdery feel even when it is used at high contents, in particular at total 1,4:3,6-dianhydrohexitol contents of greater than or equal to 10% by dry weight relative to the total weight of the composition. Thus, the 1,4:3,6-dianhydrohexitol content of the preparation for topical use is advantageously greater than or equal to 10%, preferably greater than or equal to 15%, more preferably greater than or equal to 20% by dry weight relative to the total weight of the preparation. Advantageously, this content will not exceed 40%, preferably 30% and more preferentially still 25% by dry weight relative to the total weight of the preparation.

The invention also relates to a preparation for topical use comprising a moisturizing agent, said moisturizing agent being a composition comprising at least one 1,4:3,6-dianhydrohexitol, as described above. As indicated above, this composition may in particular be free of glycerol.

Another subject of the invention is a method for moisturizing the skin comprising the application to the surface of the skin of a preparation for topical use as described above.

Naturally, other embodiments of the invention could have been envisaged by a person skilled in the art without thereby departing from the scope of the invention defined by the claims hereinbelow.

The invention will now be illustrated in the nonlimiting examples hereinbelow.

EXAMPLES

Example 1

Various polyols were incorporated into a body milk as preparation for topical use. 5 panelists evaluated the feel on the skin after application of each of the formulae after spreading 0.2 g of product over a surface area of 1 cm×5 cm on the forearm, spreading by 10 rotations and a waiting time of 2 minutes.

The composition of the lotion was the following (% by weight/total weight):

| Phase | INCI name | Function | % |
|---|---|---|---|
| A | Tocopherol | Antioxidant | 0.02 |
|  | Stearic acid & palmitic acid | Surfactant | 5.00 |
|  | Glyceryl stearate | Texturant | 5.50 |
|  | Sunflower seed oil | Emollient | 10.0 |
| B | Aqua (water) | Solvent | 57.98 |
|  | Triethanolamine | Neutralizer | 0.50 |
|  | Phenoxyethanol & Chlorphenesin & Glycerol | Preservative | 1.00 |
|  | Polyol (expressed as solids content) | Moisturizer | 20.00 |
|  |  |  | 100.00 |

Procedure

1/ With magnetic stirring, separately prepare the mixtures A and B, heat to 70° C.

2/ Add A to B with a rotor stator for 2 minutes then pass the mixture into a deflocculator with gentle stirring.

The results of the tests are summarized in table 1:

TABLE 1

| Polyol | Feel on the skin |
|---|---|
| Glycerol (99.9%) | greasy and tacky |
| Xylitol (XYLISORB ® 300) | greasy and tacky |
| Sorbitol (NEOSORB ® P 60W) | greasy and tacky |
| Maltitol (SWEETPEARL ® P200) | greasy and tacky |
| Isosorbide (POLYSORB ® LP sold by the Applicant (1)) | non-greasy and non-tacky; dry and powdery |

(1): Appearance: colorless and completely odor-neutral transparent liquid - Solids content: 80% - Purity: 99.5% minimum of isosorbide relative to the solids content - Impurities: less than 0.5% relative to the solids content - pH in aqueous solution at 40% of 7.5.

These results clearly show that among the polyols tested only isosorbide makes it possible to obtain a body milk with neither a greasy nor tacky feel. Furthermore, isosorbide imparts a very pleasant dry and powdery feel to the skin.

Example 2

The moisturizing efficiency of isosorbide was compared to that of sorbitol, xylitol, betaine and glycerol. For this, these polyols were incorporated into a cosmetic preparation for topical use in gel form.

The composition of the gel was the following (% by weight/total weight): 6% by weight of isosorbide, sorbitol, xylitol, betaine or glycerol and 1% by weight of gelling carbomer in water. The placebo consists only of 1% by weight of gelling carbomer in water.

The moisturizing efficiency of each of the preparations for topical use was evaluated by corneometry. Corneometry is a scientifically recognized method for measuring the hydration of the surface layers of the skin. It is based on the determination of the capacitance of the superficial stratum corneum.

The study was carried out with ten healthy volunteers aged from 18 to 65 years old. The moisturizing efficiency of each of the five formulae was evaluated 1 hour, 2 hours and 4 hours after its application in the laboratory on the inner face of the forearm. The evaluation was carried out by comparing the hydration levels of the zone on which the product was applied after 1 hour (T1h), 2 hours (T2h) and 4 hours (T4h) with the hydration level measured before application of the product (T0).

For each formula, an amount of around 2 mg/cm$^2$ was applied to an area of 3×3 cm, in non-occlusive epicutaneous mode. In addition to the zones treated with the five formulae, two additional zones were evaluated: one treated with a placebo and the other without treatment for the duration of the study.

The measurements were carried out with a Corneometer® CM285 included in a Multiprobe Adapter System MPA® (Courage-Khazaka GmbH, Germany). The instrument determines the capacitance of the epidermis, which is proportional to the water content thereof, at a depth of around 15 μm. This method is based on the difference between the electrical permittivity of the water which is 81 and that of other substances (<7). The probe of the Corneometer (surface area of 49 mm$^2$) is positioned perpendicular to the test area which was delimited beforehand with a pencil. The measurement of the capacitance lasts 1 second. Each measurement is carried out twice and the average of the two measurements is noted. The instrument gives the values in arbitrary units ranging from 0 to 130, with an error margin of ±3%.

Each volunteer rested for around 1 minute in an air-conditioned room before each measurement with the Corneometer® in order to avoid abnormal results due to excessive perspiration or stress.

Table 2 below reports the mean hydration values expressed in arbitrary units (AU). The variations of the hydration between T0 and T1h, T2h and T4h respectively are given in table 3.

TABLE 2

| TIME | Sorbitol | Xylitol | Isosorbide | Betaine | Glycerol | Placebo | Untreated |
|---|---|---|---|---|---|---|---|
| T0 | 48.60 | 45.94 | 46.54 | 43.39 | 42.03 | 45.58 | 49.17 |
| T1 h | 54.16 | 55.37 | 56.60 | 55.61 | 57.05 | 38.84 | 45.47 |
| T2 h | 49.11 | 52.68 | 52.88 | 54.30 | 56.15 | 38.06 | 45.51 |
| T4 h | 46.91 | 45.28 | 52.50 | 50.74 | 56.57 | 38.39 | 47.05 |

TABLE 3

Mean variations in % (1)

| TIME | Sorbitol | Xylitol | Isosorbide | Betaine | Glycerol | Placebo | Untreated |
|---|---|---|---|---|---|---|---|
| T1 h vs T0 | 11.4 | 20.5 | 21.6 | 28.2 | 35.7 | −14.8 | −7.5 |

TABLE 3-continued

| | Mean variations in % (1) | | | | | | |
|---|---|---|---|---|---|---|---|
| TIME | Sorbitol | Xylitol | Isosorbide | Betaine | Glycerol | Placebo | Untreated |
| T2 h vs T0 | 1.0 | 14.7 | 13.6 | 25.1 | 33.6 | −16.5 | −7.4 |
| T4 h vs T0 | −3.5 | −1.4 | 12.8 | 16.9 | 34.6 | −15.8 | −4.3 |

(1) T . . . h-T0/T0 * 100

It is remarkable and surprising to note that not all the polyols have the same effect both from the point of view of instantaneous hydration (in the short term, i.e. at 1 h) and maintenance of the hydration over time (i.e. at 2 h or 4 h). Most of the polyols with the exception of isosorbide do not make it possible to maintain hydration of the skin over time. Only isosorbide makes it possible to obtain a very good compromise between short-term hydration and maintenance of the hydration over time (T4h vs T0). From this point of view isosorbide gives the gel a satisfactory moisturizing power, comparable to that of betaine.

Example 3

A blind discriminant sensory analysis on two body milks as preparation for topical use, one with isosorbide as moisturizing agent the other with glycerol, was carried out with 37 panelists, experts in textural sensory analysis.

The compositions of the two body milks evaluated correspond to those given in example 1.

Implementation of the Test

The two body milks are provided as comparison and randomized for each panelist. Two pairs of products are evaluated per session.

For each product, the panelist must evaluate the following descriptors at the surface of the epidermis: fresh, spreading, greasy, tacky, soft, penetration.

Each panelist notes the descriptors on a scale between 0 and 10.

Evaluation Protocol

The forearms are washed beforehand. Next, two application zones having a surface area of 5 cm² (1×5) are drawn on the forearm of each panelist for the evaluation of the products. 0.2 g of each product is applied to the delimited zone in order to be evaluated.

The criteria for evaluating the descriptors linked to the spreading of the product are given in table 4 below and those linked to the feel in tables 5 and 6 respectively.

TABLE 4

| DESCRIPTOR | GESTURE | DEFINITION |
|---|---|---|
| FRESH | Examination after application of 0.2 g by the leader panel on the forearm, by carrying out 10 rotations | Up to the $2^{nd}$ rotation, the product provides a feeling of freshness, comparable to fresh water on the skin. |
| SPREADING | | From the $5^{th}$ to the $10^{th}$ rotation, the product does not put up resistance to the spreading, and is distributed on the skin in a homogeneous layer. |

TABLE 5

| DESCRIPTOR | GESTURE | DEFINITION |
|---|---|---|
| GREASY | Examination 1 minute after application and spreading by 10 rotations | By pinching the skin between the thumb and index finger, the presence of a thickness of product is felt. |
| TACKY | | By patting the skin with the index finger, an adhesion is felt: the product hinders the movement. |

TABLE 6

| DESCRIPTOR | GESTURE | DEFINITION |
|---|---|---|
| PENETRATING | Examination 2 minutes after application and spreading by 10 rotations | By sliding over the skin, the product disappeared and no residue is recovered. |
| SOFT | | By stroking the skin, the feel is dry and slippy, the skin is softer than in the natural state. |

The average for each descriptor for each of the two body milks is given in table 7.

TABLE 7

| Variables evaluated | Isosorbide body milk Averages | Glycerol body milk Averages |
|---|---|---|
| FRESH | 4.85 | 4.4 |
| SPREADING | 7.7 | 7.45 |
| GREASY | 6.45 | 6.8 |
| TACKY | 2.85 | 3.45 |
| SOFT | 5.85 | 5.65 |
| PENETRATING | 7.95 | 7.7 |

These results show that the body milk containing isosorbide as moisturizing agent is significantly less tacky and greasy than the comparative body milk containing glycerol. Furthermore, it spreads better, provides a greater feeling of freshness, is softer and more penetrating. In conclusion, the use of isosorbide as a complete replacement for glycerol results in the sensory advantages desired by the consumer that glycerol is not able to provide.

The invention claimed is:

1. A method for moisturizing the skin of a subject in need thereof, comprising the step of administering a composition comprising a moisturizing agent, to said subject and thereby moisturizing the skin of the subject, and wherein the moisturizing agent is at least one 1,4:3,6-dianhydrohexitol and the preparation has a glycerol content of less than or equal to 10% by weight relative to the total weight of the composition.

2. The method as claimed in claim 1, wherein the 1,4:3,6-dianhydrohexitol is isosorbide.

3. The method as claimed in claim 1, wherein the composition comprising at least one 1,4:3,6-dianhydrohexitol is used in liquid form, optionally with a solids content of between 75% and 85%.

4. The method as claimed in claim 1, wherein the composition comprising at least one 1,4:3,6-dianhydrohexitol is in solid form, optionally in crystalline form or in the form of powder or flakes.

5. The method as claimed in claim 1, wherein the composition comprising at least one 1,4:3,6-dianhydrohexitol is incorporated into topical preparation.

6. The method as claimed in claim 5, wherein the topical preparation is a cosmetic preparation, a pharmaceutical preparation or a veterinary preparation.

7. The method as claimed in claim 5, wherein the topical preparation is free of glycerol.

8. The method as claimed in claim 1, wherein the preparation for topical method has a 1,4:3,6-dianhydrohexitol content of between 0.1% and 50% by dry weight relative to the total weight of the preparation.

9. The method according to claim 1, wherein said subject is a human or animal.

10. The method as claimed in claim 1, wherein the topical preparation has a glycerol content of less than or equal to 5% or less than or equal to 1% by weight relative to the total weight of the composition.

11. The method as claimed in claim 8, wherein the preparation for topical method has a 1,4:3,6-dianhydrohexitol content of between 1% and 40%, between 5% and 30%, or between 10% and 25% by dry weight relative to the total weight of the preparation.

12. The method as claimed in claim 1, wherein the hydratation level of the skin is increased in the first hour after the administration.

13. The method as claimed in claim 1, wherein the 1,4:3,6-dianhydrohexitol is isomannide.

14. The method as claimed in claim 1, wherein the 1,4:3,6-dianhydrohexitol is isoidide.

\* \* \* \* \*